United States Patent [19]
Durant et al.

[11] 3,975,530
[45] Aug. 17, 1976

[54] N-CYANO-N'-HETEROCYCLIC-ALKYL QUANIDINE INHIBITORS OF H₂ HISTAMINE RECEPTORS

[75] Inventors: Graham John Durant, Welwyn Garden City; John Colin Emmett, Codicote; Charon Robin Ganellin, Welwyn Garden City, all of England

[73] Assignee: Smith Kline & French Laboratories Limited, Welwyn Garden City, England

[22] Filed: Apr. 18, 1975

[21] Appl. No.: 569,717

Related U.S. Application Data

[62] Division of Ser. No. 385,027, Aug. 2, 1973, Pat. No. 3,897,444.

[30] Foreign Application Priority Data
Sept. 5, 1972  United Kingdom............... 41160/72
Feb. 8, 1973   United Kingdom................ 6154/73

[52] U.S. Cl.................. 424/270; 424/250; 424/251; 424/263; 424/269; 424/272; 424/273
[51] Int. Cl.².......................... A61K 31/425
[58] Field of Search........... 424/250, 251, 263, 269, 424/270, 272, 273

[56] References Cited
UNITED STATES PATENTS
3,036,083   5/1962   Mull................................ 260/294.9
3,074,955   1/1963   Shapiro............................... 260/295

*Primary Examiner*—Norman A. Drezin
*Attorney, Agent, or Firm*—Joan S. Keps; Richard D. Foggio; William H. Edgerton

[57] ABSTRACT

N-Cyano-N'-heterocyclic-alkylguanidinos which are inhibitors of histamine activity.

11 Claims, No Drawings

N-CYANO-N'-HETEROCYCLIC-ALKYL QUANIDINE INHIBITORS OF H₂ HISTAMINE RECEPTORS

This is a division of application Ser. No. 385,027 filed Aug. 2, 1973, now U.S. Pat. No. 3,897,444.

This invention relates to pharmacologically active compounds, in particular to pharmacologically active N-cyano-N'-heterocyclic alkylguanidines, and pharmaceutical compositions and methods of inhibiting H-2 histamine receptors with these compounds. The compounds of the invention can exist as the addition salts, but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated as H-1. A further group of substances has recently been described by Black et. al., (Nature 1972, 236, 385) which are distinguished by the fact that they act at histamine receptors other than the H-1 receptor and these other receptors have been designated as H-2 receptors. This latter group of substances, to certain of which the present invention relates, are thus of utility in inhibiting certain actions of histamine which are not inhibited by the above-mentioned "antihistamines". The substances of this invention may also be of utility as inhibitors of certain actions of gastrin.

Throughout the present specification and claims, by the term "lower alkyl" we mean an alkyl group containing from 1 to 4 carbon atoms. The cyanoguanidines with which the present invention is concerned may be represented by the following general formula:

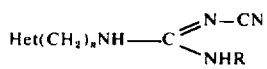

FORMULA I wherein R is hydrogen or lower alkyl such as methyl; $n$ is from 3 to 5; and Het is a nitrogen containing 5 or 6 membered heterocyclic ring such as imidazole, pyridine, thiazole, isothiazole, oxazole, isoxazole, pyrazole, triazole, thiadiazole, pyrimidine, pyrazine or pyridazine which is optionally substituted by lower alkyl, trifluoromethyl, hydroxyl, halogen or amino, or pharmaceutically acceptable acid addition salts thereof.

It will be understood that the structure illustrated in Formula I is only one of several representations and that other tautomeric forms are also covered by the present invention.

In a preferred group of compounds R is methyl. Het is preferably imidazole or thiazole. Particularly useful specific compounds are N-cyano-N'-methyl-N''-[4-(4-imidazolylbutyl)]guanidine, N-cyano-N'-methyl-N''-[3-(4-imidazolylpropyl)]guanidine and N-cyano-N'-methyl-N''-[4-(2-thiazolylbutyl)]guanidine.

The compounds of the present invention may be produced from an amine of the formula Het—(CH₂)ₙ—NH₂, wherein Het and $n$ have the same significance as in Formula I by reaction thereof with an isothiourea or isourea of formulae II:

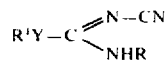

FORMULA II wherein R has the same significance as in Formula I, Y is sulphur or oxygen (preferably sulphur) and R¹ is lower alkyl (preferably methyl). This reaction may be carried out in the absence of a solvent but preferably is carried out in a solvent such as acetonitrile.

Alternatively, for those compounds of Formula I wherein R is preferably lower alkyl, a thiourea of Formula III:

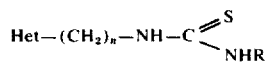

FORMULA III wherein Het, $n$ and R have the same significance as in Formula I may be reacted with a heavy metal salt of cyanamide such as the lead, mercury or cadmium salt. This process may be conveniently carried out in a solvent such as acetonitrile or dimethylformamide. In a modification of this process the thiourea of Formula III is first reacted with a desulphurising agent such as a heavy metal salt or oxide and then treated with cyanamide.

An advantageous method for the production of compounds of Formula I is by the reaction of an amine of Formula Het (CH₂)ₙNH₂ with a cyanodithioimidocarbonate or a cyanoimidocarbonate of Formula IV:

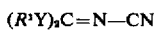

FORMULA IV wherein $R^1$ is alkyl, preferably methyl and $Y$ is sulphur or oxygen, preferably sulphur to give an N-cyanoisothiourea or N-cyanoisourea of Formula V.

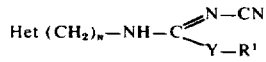

FORMULA V wherein Het and $n$ have the same significance as in Formula I and Y and R¹ have the same significance as in Formula IV. Subsequent reaction of the compounds of Formula V with R NH₂ leads to the production of cyanoguanidines of Formula I. Both stages of this reaction may be carried out in a solvent such as ethanol or isopropyl alcohol. In a modification of this method, the compound of Formula IV, which in the preferred case is dimethylcyanodithioimidocarbonate, may be reacted sequentially with Het(CH₂)ₙ NH₂ and R NH₂ without isolation of the intermediate compound of Formula V. In an alternative method for the production of those compounds of Formula I wherein R is hydrogen, the amine of Formula Het(CH₂)ₙNH₂ may be reacted with a metal salt of dicyanamide of formula MN (CN)₂ wherein M is a metal e.g., an alkali metal such as sodium in an appropriate solvent and in the presence of an equivalent amount of a strong acid.

As stated above, the compounds represented by Formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane at doses of from 2 to 256 micromoles per kilogram intravenously. Similarly, the action of these compounds may, in many cases, be demonstrated by their antagonism to the effects of histamine on other tissues which, according to the above-mentioned paper of Black et. al., are H-2 receptors.

Examples of such tissues are perfused isolated guinea-pig heart, isolated guinea-pig right atrium and isolated rat uterus. The compounds of the invention have also been found to inhibit the secretion of gastric acid stimulated by pentagastrin or by food. In addition to the above the compounds of the invention also show some anti-inflammatory activity in conventional tests.

The level of activity found for the compounds of the present invention is illustrated by the effective dose range in the anaesthetised rat, as mentioned above, of from 2 to 256 micromoles per kilogram, given intravenously. Many of the compounds of the present invention produce a 50% inhibition in this test at a dose of from 3 – 15 micromoles per kilogram.

Pharmaceutical compositions comprising a pharmaceutical carrier and a compound of Formula I or a pharmaceutically acceptable acid addition salt thereof and methods of inhibiting H-2 histamine receptors which comprise administering to an animal a compound of Formula I or a pharmaceutically acceptable acid addition salt thereof are also objects of this invention.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredient will preferably be administered in equal doses one to three times per day. The daily dosage regimen will preferably be from about 150 mg. to about 750 mg., most preferably from about 300 mg. to about 600 mg.

For therapeutic use, the pharmacologically active compounds of the present invention will normally be administered as a pharmaceutical composition comprising as the or an essential active ingredient aat least one such compound in the basic form or in the form of an addition salt with a pharmaceutically acceptable acid and in association with a pharmaceutical carrier therefor. Such addition salts inclulde those with hydrochloric, hydrobromic, hydriodic, sulphuric, picric and maleic acids.

Other pharmacologically active compounds may in certain cases be included in the composition. Advantageously the compositions will be made up in a dosage unit form appropriate to the desired mode of administration, for example as a tablet, capsule, injectable solution or as a cream for topical administration.

The invention is illustrated but in no way limited by the following examples:

EXAMPLE 1

N-Cyano-N'-methyl-N''-[4-(4-imidazolylbutyl)]guanidine

Lead cyanamide (30 g.) was added to a solution of N-methyl-N'-(4-(4-imidazolyl butyl)thiourea (21.2 g.) in acetonitrile (300 ml) containing dimethylformamide (50 ml.). The suspension was stirred under reflux for 24 hours, fresh lead cyanamide (15 g.) was added and the suspension was then stirred under reflux for an additional 24 hours. Following filtration and concentration the product was chromatographed on a column of silica gel with isopropyl alcohol as eluant to give N-cyano-N'-methyl-N''-[4-imidazolylbutyl)]guanidine (9.4 g.), m.p. 147°–148° (from water).

(Found: C, 54.2; H, 7.2; N, 37.7. $C_{10}H_{16}N_6$. Requires: C, 54.5; H, 7.3; N, 38.2).

EXAMPLE 2

N-Cyano-N'-methyl-N''-(3-(4-imidazolyl)propyl)-guanidine

The reaction of N-methyl-N'-(3-(4-imidazolyl propyl)thiourea (7.0 g.) with lead cyanamide (21.8 g.) under conditions similar to those described in Example 1 afforded N-cyano-N'-methyl-N''-(3-(4-imidazolyl)-propyl)guanidine (1.5 g. m.p. 155°–156°) following chromatography on silica gel with ethyl acetate-isopropyl alcohol (2:1) as eluant and recrystallisation from water.

(Found: C, 52.0; H, 6.7; N, 40.8 $C_9H_{14}N_6$. requires: C, 52.4; H, 6.8; N, 40.8).

EXAMPLE 3

N-Cyano-N'-methyl-N''-[4-(2-thiazolyl)butyl]guanidine

A solution of 2-(4-aminobutyl)thiazole (from the dihydrochloride 13.8 g.) and N-cyano-N', S-dimethylisothiourea (7.75 g) in acetonitrile was heated under reflux for 24 hours. Following concentration, the residue was chromatographed on a column of silica gel with acetonitrile as eluant and the product obtained was recrystallised from isopropyl alcohol-isopropyl acetate to yield N-cyano-N'-methyl-N''-[4-(2-thiazolyl)butyl]guanidine m.p. 87°–89.5°.

(Found: C, 50.7; H, 6.5; N, 0b 29.8; S, 13.5. $C_{10}15N_5S$. requires: C, 50.6; H, 6.4; N, 29.5; S, 13.5)

EXAMPLE 4

Reaction of the following amines:
a. 3-bromo-2-(4-aminobutyl)pyridine
b. 3-(4-aminobutyl)isothiazole
c. 2-(4-aminobutyl)oxazole
d. 3-(4-aminobutyl)isoxazole
e. 3-(4-aminobutyl)pyrazole
f. 3-(4-aminobutyl)-1,2,4-triazole
g. 5-amino-2-(4-aminobutyl)-1,3,4-thiadiazole
h. 2-(4-aminobutyl)pyrimidine
i. 2-(4-aminobutyl)pyrazine
j. 3-(4-aminobutyl)pyridazine
k. 4-methyl-5-(4-aminobutyl)imidazole
l. 3-hydroxyl-2-(4-aminobutyl)pyridine
m. 4-trifluoromethyl-5-(4-aminobutyl)imidazole
n. 4-(5-aminopentyl)imidazole with dimethylcyanodithioimidocarbonate at room temperature overnight in ethanol followed by addition to the reaction mixture of ethanolic methylamine yielded respectively the following products.

a. N-cyano-N'-methyl)-N''-[4-(3-bromo-2-pyridyl)butyl]guanidine
b. N-cyano-N'-methyl-N''-[4-(3-isothiazolyl)butyl]-guanidine.
c. N-cyano-N'-methyl-N''-[4-(2-oxazolyl)butyl]-guanidine.
d. N-cyano-N'-methyl-N''-[4-(3-isoxazolyl)butyl]-guanidine.
e. N-cyano-N'-methyl-N''-[4-(3-pyrazolyl)butyl]-guanidine.
f. N-cyano-N'-methyl-N''-[4-(3-1,2,4-triazolyl)-butyl]guanidine.
g. N-cyano-N'-methyl-N''-[4-(5-amino-2-1,3,4-thiadiazolyl)butyl]guanidine
h. N-cyano-N'-methyl-N''-[4-(2-pyrimidyl)butyl]-guanidine.
i. N-cyano-N'-methyl-N''-[4-(2-pyrazinyl)butyl]-guanidine.
j. N-cyano-N'-methyl-N''-[4-(3-pyridazyl)butyl]guanidine
k. N-cyano-N'-methyl-N''-[4-(4-methyl-5-imidazolyl)butyl]guanidine.
l. N-cyano-N'-methyl-N''-[4-(3-hydroxyl-2-pyridyl)butyl]guanidine.
m. N-cyano-N'-methyl-N''-[4-(4-trifluoromethyl-5-imidazolyl)butyl]guanidine.
n. N-cyano-N'-methyl-N''-[5-(4-imidazolyl)pentyl]-guanidine.

EXAMPLE 5

Reaction of the amines set out in Example 4 with dimethylcyanodithioimidocarbonate at room temperature overnight in ethanol followed by addition to the reaction mixture of butylamine, ethylamine or of ammonia resulted respectively in the corresponding compounds of Formula I wherein R is butyl, ethyl or hydrogen.

EXAMPLE 6

| INGREDIENTS | AMOUNTS |
| --- | --- |
| N-cyano-N'-methyl-N''-[4-(4-imidazolylbutyl)]guanidine | 150 mg. |
| Sucrose | 75 mg. |
| Starch | 25 mg. |
| Talc | 5 mg. |
| Stearic Acid | 2 mg. |

The ingredients are screened, mixed and filled into a hard gelatin capsule.

We claim:

1. A pharmaceutical composition to inhibit H-2 histamine receptors comprising a pharmaceutical carrier and in an effective amount to inhibit H-2 histamine receptors a guanidine compound of the formula:

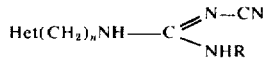

wherein R is hydrogen or lower alkyl; n is from 3 to 5; and Het is an unsaturated heterocyclic nucleus selected from, the group consisting of imidazole, thiazole, isothiazole, oxazole, isoxazole, pyrazole, triazole, thiadiazole, pyrimidine, pyrazine and pyridazine which nucleus is attached through a carbon atom in said nucleus adjacent to a nitrogen atom and is unsubstituted or monosubstituted by lower alkyl, trifluoromethyl, hydroxyl, halogen or amino, or a pharmaceutically acceptable acid addition salt thereof.

2. The pharmaceutical composition of claim 1 wherein R is methyl.

3. The pharmaceutical composition of claim 1 wherein Het is imidazole or thiazole attached through a carbon atom in said nucelus adjacent to a nitrogen atom.

4. The pharmaceutical composition of claim 1 wherein the guanidine compound is N-cyano-N'-methyl-N''-[4-(4-imidazolylbutyl)]-guanidine.

5. The pharmaceutical composition of claim 1 wherein the guanidine compound is N-cyano-N'-methyl-N''-[3-(4-imidazolylpropyl)]guanidine.

6. The pharmaceutical composition of claim 1 wherein the guanidine compound is N-cyano-N'-methyl-N''-[4-(2-thiazolylbutyl)]guanidine.

7. A method of inhibiting H-2 histamine receptors which comprises administering to an animal in an effective amount to inhibit H-2 histamine receptors a guanidine compound of the formula:

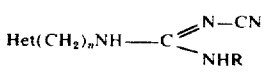

FORMULA I wherein R is hydrogen or lower alkyl; n is from 3 to 5; and Het is an unsaturated heterocyclic nucleus selected from the group consisting of imidazole, pyridine, thiazole, isothiazole, oxazole, isoxazole, pyrazole, triazole, thiadiazole, pyrimidine, pyrazine and pyridazine which nucleus is attached through a carbon atom in said nucleus adjacent to a nitrogen atom and is unsubstituted or monosubstituted by lower alkyl, trifluoromethyl, hydroxyl, halogen or amino, or a pharmaceutically acceptable acid addition salt thereof.

8. The method of claim 7 wherein the guanidine compound is N-cyano-N'-methyl-N''-[4-(4-imidazolybutyl)]guanidine.

9. The method of claim 7 wherein the guanidine compound is N-cyano-N′-methyl-N″-[3-(4-imidazolylpropyl)]guanidine.

10. The method of claim 7 wherein the guanidine compound is N-cyano-N′-methyl-N″-[4-(2-thiazolylbutyl)]guanidine.

11. A method of inhibiting gastric acid secretion which comprises administering internally to an animal in need of inhibition of gastric acid secretion in an effective amount to inhibit gastric acid secretion a guanidine compound of the formula:

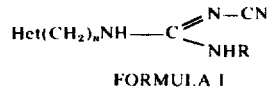

FORMULA I wherein R is hydrogen or lower alkyl; $n$ is from 3 to 5; and Het is an unsaturated heterocyclic nucleus selected from the group consisting of imidazole, pyridine, thiazole, isothiazole, oxazole, isoxazole, pyrazole, triazole, thiadiazole, pyrimidine, pyrazine and pyridazine which nucleus is attached through a carbon atom in said nucleus adjacent to a nitrogen atom and is unsubstituted or monosubstituted by lower alkyl, trifluoromethyl, hydroxyl, halogen or amino, or a pharmaceutically acceptable acid addition salt thereof.

* * * * *